United States Patent [19]

Steiner et al.

[11] Patent Number: 4,885,278
[45] Date of Patent: Dec. 5, 1989

[54] 5-SUBSTITUTED 10-CYANOMETHYLENETHIENO(3,4-B)BENZAZEPINES

[75] Inventors: Gerd Steiner, Kirchheim; Hans-Juergen Teschendorf, Dudenhofen; Liliane Unger, Ludwigshafen; Rudolf Binder, Worms, all of Fed. Rep. of Germany

[73] Assignee: BASF Aktiengesellschaft, Ludwigshafen, Fed. Rep. of Germany

[21] Appl. No.: 196,605

[22] Filed: May 20, 1988

[30] Foreign Application Priority Data

May 21, 1987 [DE] Fed. Rep. of Germany ....... 3717069

[51] Int. Cl.$^4$ .................... C07D 495/04; A61K 31/55
[52] U.S. Cl. ...................................... 514/215; 540/586
[58] Field of Search .......................... 540/586; 514/215

[56] References Cited

U.S. PATENT DOCUMENTS 4,362,727 12/1982 Steiner ................................. 540/586
4,388,237 6/1983 Steiner ................................. 540/586
4,745,111 5/1988 Steiner ................................. 540/586

OTHER PUBLICATIONS

*Drug Research*, 25, 712 (1975).

*Primary Examiner*—Robert Gerstl
*Attorney, Agent, or Firm*—Oblon, Spivak, McClelland, Maier & Neustadt

[57] ABSTRACT

Compounds of the formula

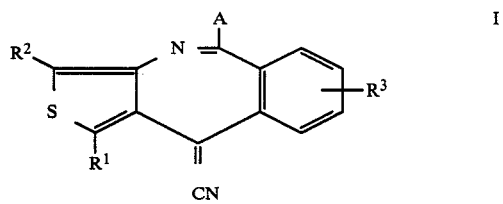

where $R^1$, $R^2$, $R^3$ and A have the meanings stated in the specification, as well as the use thereof for controlling diseases, are described.

7 Claims, No Drawings

5-SUBSTITUTED 10-CYANOMETHYLENETHIENO(3,4-B)BEN-ZAZEPINES

The present invention relates to 10-cyanomethylenethieno[3,4-b]benazepines substituted in the 5-position, to a process for the preparation thereof, and to the use thereof as drugs which can be employed as sedatives, hypnotics, tranquilizers, muscle relaxants, neuroleptics or antiparkinson agents.

It is known that tricyclic ring systems with a dibenzo structure to a central heterocyclic 7-ring, which may have a basic side radical, eg. an N-methylpiperazino radical, have neuroleptic effects. Examples of such tricyclics are N-methylpiperazine derivatives of dibenzo[b,e][1,4]diazepines (clozapine), dibenzo[b,f][1,4]-thiazepines (clotiapine), dibenzo[b,f][1,4]oxazepines (loxapine) or morphanthridines (perlapine), as are disclosed, for example, in the compilation of J. Schmutz in Arzneim-Forsch. 25 (1975), 712–720.

German laid-open applications DOS 2,918,778, DOS 3,037,971 and DOS 3,524,744 describe 6-substituted 11-alkylenemorphanthridines, 5-substituted 9-cyanomethylenedithieno[3,4-b:4′,3-e]azepines and 4-substituteed 10-cyanomethylenethieno[4,3-e]benzazepines with valuable pharmacological properties.

We have now found that 5-substituted 10-cyanomethylenethieno[3,4-b]benzazepines of the formula I

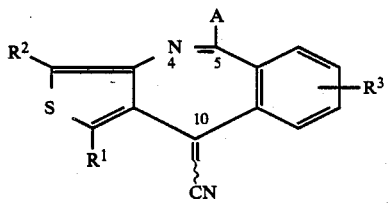

where $R^1$, $R^2$ and $R^3$ are each hydrogen or halogen or alkyl of 1 to 3 carbon atoms, A is an amino radical —$NR^4R^5$ where $R^4$ and $R^5$ form, together with the nitrogen connecting them, a 5- to 7-membered saturated ring which may contain a nitrogen or oxygen as further hetero atom, it being possible for an additional nitrogen to be substituted by alkyl of 1 to 3 carbon atoms, hydroxyalkyl of 2 or 3 carbon atoms, alkoxyalkyl where alkyl or alkoxy is of 2 or 3 carbon atoms, cycloalkyl or cycloalkylmethyl with 3 to 7 carbon atoms in the cycloalkyl ring, alkynyl of 2 to 5 carbon atoms and additionally by oxygen in the form of an N-oxide, or A is an amino radical —$NHR^6$ where $R^6$ is aminoalkyl of 2 to 7 carbon atoms, it being possible for the amine nitrogen to be substituted by lower alkyl of 1 to 5 carbon atoms or to be a constituent of a 5- to 7-membered saturated ring which may contain a nitrogen or oxygen as further hetero atom, it being possible for a nitrogen which is present to be substituted by lower alkyl of 1 to 3 carbon atoms or hydroxyalkyl of 2 or 3 carbon atoms, and the physiologically tolerated acid addition salts thereof have valuable pharmacological properties.

Particularly suitable meanings for $R^1$, $R^2$ and $R^3$ are the following: hydrogen, fluorine, chlorine and methyl.

An —$NR^4R^5$ amino radical A is preferably piperazinyl, homopiperazinyl, piperidinyl or morpholinyl.

Particularly preferred —$NR^4R^5$ are 4-methylpiperazinyl, the 4-oxide of 4-methylpiperazinyl, 4-ethylpiperazinyl and N-methylhomopiperazinyl.

In the amino radical —$NHR^6$, $R^6$ is preferably 2-dimethylaminoethyl or 2-piperidin-1-ylethyl.

It is to be noted that the novel compounds of the formula I exist as (E) and (Z) isomers Ia and b.

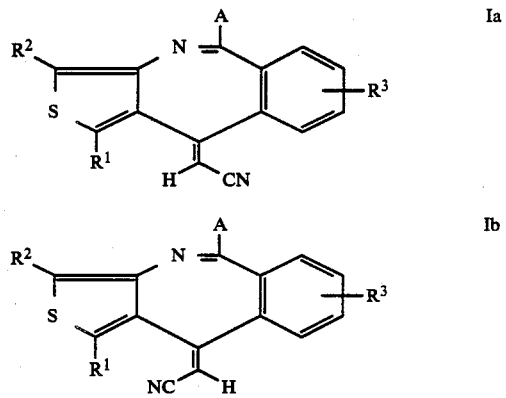

The (E) and (Z) isomers can be separated, for example, by fractional crystallization or by column chromatography.

The following compounds are particularly preferred:
(E),(Z)-10-cyanomethylene-5-(4-methyl-1-piperazinyl)-thieno[3,4-b]benzazepine
(E)-10-cyanomethylene-5-(4-methyl-1-piperazinyl)-thieno[3,4-b]benzazepine
(Z)-10-cyanomethylene-5-(4-methyl-1-piperazinyl)-thieno[3,4-b]benzazepine As the Examples show, in individual cases the (E) and (Z) isomers can be separated without excessive effort.

The novel compounds of the formula I are prepared by reacting a compound of the formula II

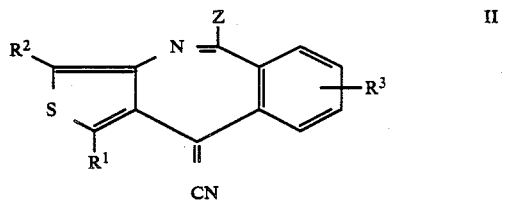

where $R^1$, $R^2$ and $R^3$ have the stated meanings, and Z is a nucleofugic leaving group, with a nucleophile AH, in which A has tthe meanings stated for formula I, where appropriate separating into the pure cis and trans isomers and/or where appropriate converting the resulting compound into the N-oxide and/or into the acid addition salt of a physiologically tolerated acid.

Suitable nucleofugic leavinng groups for Z are halogens, in particular bromine or chlorine. The reaction is expediently carried out in the presence of an excess of the amine AH used, which simultaneously acts as solvent and, where appropriate, as acid-binding agent. It is possible, where appropriate, to operate in the presence of an inert solvent such as a cyclic saturated ether, especially tetrahydrofuran or dioxane, of benzene or of a benzene hydrocarbon such as toluene, xylene, mesitylene or decahydronaphthalene, or of an aprotic polar solvent such as diemthylformamide. If only one equivalent of the amine AH is used, it is necessary also to add one equivalent of an inert base such as, for example, triethylamine.

The reaction is usually carried out at 80° to 150° C. and is generally complete within 1 to 10 hours. It may be advantageous to exclude atmospheric oxygen and to work under an inert gas, for example uner nitrogen.

The nucleophile AH is advantageously used in the reactions in a not less than 2- and up to 20-fold molar excess.

The conversion of a compound of the formula I into the N-oxide is carried out in a conventional manner, expediently using aqueous hydrogen peroxide (30% strength by weight) in ethanolic solution. The conversion into the acid addition salt of a physiologically tolerated acid is likewise carried out in a conventional manner.

The starting compounds of the formula II are obtained by refluxing a 10-cyanomethylene-4,5-dihydrothieno[3,4-b]benzazepin-5-one of the formula III

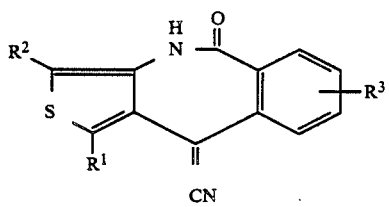

where $R^1$, $R^2$ and $R^3$ have the meanings stated for formula II, with an excess of phosphorus oxychloride, in the presence of a solvent, preferably a halohydrocarbon, and in the presence of a catalytic amount of N,N-dimethylaniline for from 1 to 5 hours, and isolating the resulting imino chloride after the excess phosphorus oxychloride has been removed by distillation and working up in an aqueous two-phase system by extraction with methylene chloride.

The novel 10-cyanomethylene-4,5-dihydrothieno[3,4-b]benzazepin-5-one of the formula III, in which $R^1$, $R^2$ and $R^3$ have the meanings stated for formula I, is prepared by forming an olefin from the carbonyl by reacting a 4,5-dihydrothieno[3,4-b]benzazepin-5,10-dione of the formula IV

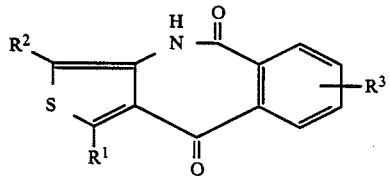

with a phosphonate of the formula Va

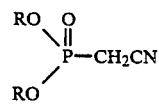

where R is alkyl of 1 to 3 carbon atoms, under the conditions of the Witting-Horner reaction in dimethylformamide in the presence of one mole-equivalent of a base, such as sodium alcoholate, at from 20° to 80° C., or with a phosphonium salt of the formula Vb

where Ph is phenyl, under the conditions of the classical Wittig reaction in dimethylformamide in the presence of one mole-equivalent of a strong base, at from 20° to 100° C.

The novel 4,5-dihydrothieno[3,4-b]benzazepine-5,10-dione of the formula IV, in which $R^1$, $R^2$ and $R^3$ have the meanings stated for formula I, is prepared by Friedel-Crafts cyclization by initially converting a 2',5'-disubstituted mono-3-thienylamide of phthalic acid, of the formula VI

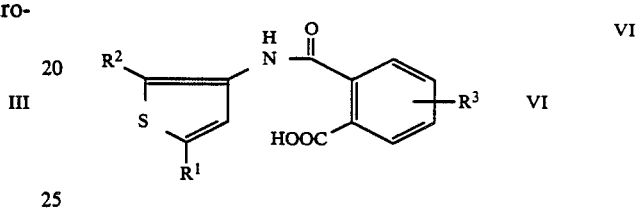

where $R^1$ and $R^2$ have the meanings stated for formula I, excepting hydrogen, with thionyl chloride in a chlorohydrocarbon, or in excess thionyl chloride without use of a solvent, at from 20° to 80° C., into the corresponding acid chloride, and then cyclizing the latter in the presence of 1 to 1.5 mole-equivalents of aluminum chloride in an inert organic solvent, such as a chlorohydrocarbon, or in a dipolar aprotic solvent, such as dimethylformamide at from 20° to 100° C.

For the conversion into the 4,5-dihydrothieno[3,4-b]benzazepine-5,10-dione of the formula IV with $R^1$ and $R^2$=H, the halogen substituents in the case where $R^1$ and $R^2$=chlorine are removed by catalytic hydrogenation in the presence of a noble metal catalyst, for example palladium on carbon, in an inert organic solvent, preferably N-methylpyrrolidone or dimethylformamide, with the addition of an acid trap such as sodium acetate or sodium hydroxide, under pressures of from atmospheric pressure to 100 bar, and at from 20° to 100° C.

The 2',5'-disubstituted mono-3-thienylamide of phthalic acid, of the formula VI, is obtained in a straight-forward manner by reacting a 2,5-disubstituted 3-aminothiophene (British Pat. No. 1,334,015) with a phthalic anhydride in an inert organic solvent such as toluene or tetrahydrofuran at room temperature for 1 to 5 hours.

The novel compounds of the formula I are usually obtained in the form of yellowish or yellow crystals and can be purified by recrystallization from the customary organic solvents, preferably from a lower alcohol, such as ethanol, or by column chromatography.

If necessary, the individual cis and trans isomers are separated by fractional crystallization in a chlorinated hydrocarbon, preferably methylene chloride, a lower monohydric alcohol, preferably methanol or ethanol, or a saturated cycloaliphatic hydrocarbon, preferably cyclohexane, or by column chromatography, in particular with methylene chloride and methanol in the ratio of from 99:1 to 85:15 parts by volume.

The free substituted 10-cyanomethylenethieno[3,4-b]benazaepines of the formula I can be converted in a conventional manner into the acid addition salt of a pharmacologically tolerated acid, preferably by adding one equivalent of the appropriate acid to a solution. Examples of pharmaceutically tolerated acids are hydrochloric acid, phosphoric acid, sulfuric acid, methanesulfonic acid, sulfamic acid, maleic acid, fumaric acid, oxalic acid, tartaric acid and citric acid.

The novel compounds have valuable pharmacological properties. They can be used as sedatives, hypnotics, tranquilizers, muscle relaxants, neuroleptics or antiparkinson agents. It is possible for one novel compound to combine several of the said types of action. In some cases, the single pure isomer obtained after separation of the isomers may preferentially exhibit an action. Hence the novel substances are suitable for the treatment of psychological disturbances, in particular schizophrenia, anxiety, excited state and disturbances of the extrapyramidal motor system, for example Parkinson's disease.

Accordingly, the invention also relates to a therapeutic agent containing a compound of the formula I or a pharmacologically tolerated acid addition salt thereof as active compound in addition to customary vehicles and diluents, as well as to the use of the novel compounds for controlling diseases.

The novel compounds can be administered in a conventional manner orally or parenterally, intravenously or intramuscularly.

The dosage depends on the age, condition and weight of the patient and on the mode of administration. As a rule, the daily dose of active compound is from about 1 to about 20 mg/kg of body weight on oral administration and from 0.1 to 2 mg/kg of body weight on parenteral administration.

The novel compounds can be used in conventional solid or liquid pharmaceutical administration forms, for example as tablets, film-coated tablets, capsules, powders, granules, sugar-coated tablets, suppositories, solutions, ointments, creams or sprays. These are prepared in a conventional manner. It is possible in this connection for the active compounds to be processed with the customary pharmaceutical auxiliaries such as tablet binders, fillers, preservatives, tablet disintegrants, flow regulators, emollients, wetting agents, dispersing agents, emulsifiers, solvents, retardants, antioxidants and/or propellant gases (cf. H. Sucker et al.: Pharmazeutische Technologie published by Thieme, Stuttgart, 1978). The administration forms obtained in this way normally contain from 0.1 to 99% by weight of the active compound.

The Examples which follow serve to illustrate the invention:

EXAMPLE 1

A. Preparation of the starting materials (a) Mono-2,5-dichloro-4-thienylamide of phthalic acid 40.0 g (196 mmol) of 2,5-dichloro-3-aminothiophene hydrochloride in 300 ml of toluene and 500 ml of water were adjusted to pH 10 with 2.5N sodium hydroxide solution, stirring vigorously. After phase separation, the insolubles were filtered off with suction, and the toluene solution of the free amine was dried and then added dropwise to a vigorously stirred mixture of 29.0 g (196 mmol) of phthalic anhydride in 100 ml of toluene at room temperature. The mixture was then stirred for 2 to 3 h and subsequently cooled in ice, and the thick precipitate of solid was filtered off with suction and thoroughly washed with toluene, and the solid was dried first in air and later in a vacuum oven. 57.6 g (93%) of melting point 169°–171° C. were obtained.

(b) 1,3-Dichloro-4,5-dihydrothieno[3,4-b]benzazepine-5,10-dione 20.0 ml (260 mmol) of thionyl chloride were added dropwise within 0.5 h to a stirred and refluxing mixture of 30.0 g (95 mmol) of mono-2,5-dichloro-3-thienylamide of phthalic acid in 450 ml of chloroform. The mixture was refluxed for a further 0.5 h and then evaporated to dryness under reduced pressure. The acid chloride which remained (29.0 g) was cautiously added a little at a time over the course of 10 to 15 min to a vigorously stirred suspension of 120 g of aluminum chloride in 18 ml of dimethylformamide at 90° C. The mixture was then stirred at 90° C. for 30 min and cautiously poured onto 2 l of ice/water. 20 ml of concentrated hydrochloric acid was added, and then the aqueous suspension was stirred for 1 h and the pale brown solid was filtered off with suction. The product was washed with $H_2O$ and then dried in a vacuum oven at 60° C. 27.8 g (98%) of product was obtained in sufficient purity for the next reaction, melting point >250° C.

(c1) 4,5-Dihydrothieno[3,4-b]benzazepine-5,10-dione 10.0 g (34 mmol) of 1,3-dichloro-4,5-dihydrothieno[3,4-b]benzazepine-5,10-dione in 450 ml of 1-methyl-2-pyrrolidone were mixed with 2.1 g of Pd/C (10%) and with 7.4 g (90 mmol) of finely powdered sodium acetate, and hydrogenation was carried out under atmospheric pressure at 50°–60° C. for 10 h. The solid was then filtered off with suction and washed with pyrrolidone and then with $H_2O$. The filtrate was then poured into 2 l of ice-water, the mixture was acidified with concentrated hydrochloric acid and then stirred for 1 h, and the solid was filtered off with suction and thoroughly washed with $H_2O$, and the crude product (3.7 g) was dried under reduced pressure.

(c2) Variant for halogen-substituted derivatives

7(8)-Chloro-4,5-dihydrothieno[3,4-b]benzazepine-5,10-dione 6.0 g (18 mmol) of 1,3,7(8)-trichloro-4,5-dihydrothieno[3,4-b]benzazepine-5,10-dione in 200 ml of n-butanol were mixed with 10.0 g (158 mmol) of ammonium formate and 2.5 g of palladium on charcoal (10%), and the mixture was refluxed for 4 h. Evaporation to dryness was followed by the residue being taken up in 150 ml of $H_2O$, and the mixture was acidified with concentrated hydrochloric acid and stirred vigorously for one hour, and then the precipitate was filtered off with suction, washed several times with $H_2O$ and dried in a vacuum oven. The crude product was taken up in 150 ml of DMF and dispersed at 100° C. The solid was filtered off with suction while hot and washed with hot DMF. 4.1 g (72%) of product were isolated and were recrystallized from glacial acetic acid. Melting point 298°–302° C.

(d) (E),(Z)-10-Cyanomethylene-4,5-dihydrothieno[3,4-b]benzazepin-5-one, mixture of (E) and (Z) isomers To prepare this product, an olefin was formed from a carbonyl of 4,5-dihydrothieno[3,4-b]benzazepine-5,10-dione by means of the Wittig-Horner reaction ($\alpha$) or by the classical Wittig synthesis ($\beta$):

($\alpha$) 10.0 g (43.7 mmol) of 4,5-dihydrothieno[3,4-b]benzazepine-5,10-dione were dissolved in 130 ml of dimethylformamide with heating, and stirred under nitrogen. Then simultaneously 9.5 g (53 mmol) of diethyl cyanomethylphosphonate and 9.5 g (55 mmol) of sodium methylate (30%) dissolved in 10 ml of dimethylformamide were slowly added dropwise (developing of color and increase in temperature indicate the start of the Wittig reaction). This mixture was then stirred at room temperaturees for 12 h, the reaction product was poured into ice-water, the mixture was acidified with concentrated hydrochloric acid, and the solid which precipitated out was filtered off with suction. The product was thoroughly washed with water and then dried under reduced pressure. Yield: 9.7 g (88%) of 10-cyanomethylene-4,5-dihydrothieno[3,4-b]benzazepin-5-one.

(β) Triphenylcyanomethylphosphonium chloride was introduced into dimethylformamide, and then 1 mole-equivalent of a 30% strength sodium methylate solution was added dropwise, or 1 mole-equivalent of sodium hydride was added, and finally 1 mole-equivalent of a solution of 4,5-dihydrothieno[3,4-b]benzazepine-5,10-dione in dimethylformamide was addded. The reaction mixture was then stirred at 50° to 80° C. for 5 to 8 h and subsequently poured onto ice/water and the mixture was extracted several times with methylene chloride. Drying and concentration of the organic phase were followed by recrystallization of the crude product from ethanol. Yield: 71% of colorless cyrstals.

In a similar manner (E),(Z)-1,3-dichloro-10-cyanomethylene-4,5-dihydrothieno[3,4-b]benzazepin-5-one was obtained by using 1,3-dichloro-4,5-dihydro-thieno[3,4-b]benzazepine-5,10-dione in the Wittig-Horner reaction and increasing the reaction temperature to 50° to 70° C., melting point >250° C.

B. Preparation of the final products (E) and (Z)-10-cyanomethylene-5-(4-methyl-1-piperazinyl)thieno[3,4-b]benzazepine.

(a) 30 ml of phosphorous oxychloride and 0.3 ml of N,N-dimethylaniline were added to 9.6 g (38 mmol) of 10-cyanomethylene-4,5-dihydrothieno[3,4-b]benzazepin-5-one (mixture of (E) and (Z)-isomers) in 60 ml of 1,1,2-trichloroethane, and the mixture was refluxed under a nitrogen atmosphere for 1.5 h. After the excess phosphorous oxychloride and dimethylaniline had been completely removed by distillation under oil pump vacuum, the residue was partitioned between methylene chloride and water, the aqueous phase was extracted twice more with methylene chloride, and the combined organic phases were washed thoroughly with dilute HCl and water. Drying and concentration of the organic phase provided 10.2 g (99%) of 5-chloro-10-cyanomethylenethieno[3,4-b]benzazepine which is sufficiently pure for the next reaction.

10.2 g (37 mmol) of 5-chloro-10-cyanomethylenethieno[3,4-b]benzazepine were dissolved in 120 ml of dimethylformamide, 10 ml (90 mmol) of N-methylpiperazine were added (highly exothermic reaction) and the mixture was stirred at 100° C. under nitrogen for 2 to 3 h. After removal of the solvent under reduced pressure, the residue was taken up in 300 ml of ice/water, the mixture was made alkaline with a little 2.5N sodium hydroxide solution and then stirred while cooling for 1 h, and the pale brown crude product was filtered off with suction, washing copiously with water. The crude product was then partitioned between methylene chloride and water, and the organic phase was worked up in a conventional manner by drying and concentrating. The crude product was purified by column chromatography (silica gel, mobile phase 95/5 methylene chloride/methanol). 8.0 g (66%) of yellowish 10-cyanomethylene-4-(4-methyl-1-piperazinyl)thieno[3,4-b]benzazepine were obtained in the form of a mixture of the (E) and (Z) isomers, melting point 146° to 150° C.

(b) To separate the (E) and (Z) isomers, 4.0 g of the mixture of isomers was digested in 40 ml of 3/1 toluene/ethanol and, after 1 h, the undissolved crystals were filtered off with suction.

The first fraction isolated was 1.2 g of yellow crystals which, according to the thin-layer chromatograph (silica gel, mobile phase 85/15 toluene/methanol), mainly cosist of the polar (Z) isomer b.

The filtrate was concentrated somewhat and from the solution slowly crystallized 1.3 g of yellow crystals which, according to the thin layer chromatogram (silica gel, mobile phase 85/15 toluene/methanl), mainly consist of the nonpolar (E) isomer a.

An additional 0.5 g of the enriched polar (Z) isomer b was obtained by concentrating the mother liquor and recrystallizing the residue from ethanol.

The (E) and (Z) isomers were obtained pure by subsequent crystallization, once or twice, of the enriched products a and be from ethanol.

Melting points: (E) isomer a 154°–156° C. (Z) isomer b 172°–173° C.

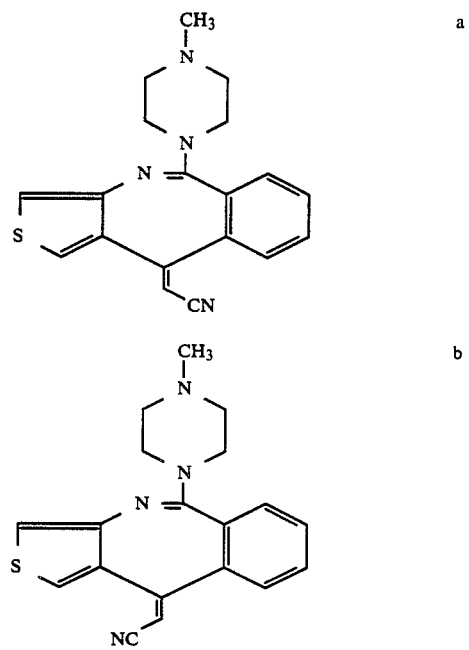

EXAMPLE 2

(E),(Z)-10-cyanomethylene-5-(4-methyl-1-piperazinyl 4-oxide)thieno[3,4-b]benzazepine.2H$_2$O 3.3 g (10 mmol) of cis,trans-10-cyanomethylene-5-(4-methyl-1-piperazinyl)-thieno[3,4-b]benzazepine (cf. Example 1) were dissolved in 100 ml of methylene chloride, and 2.2 g (10 mmol) of 3-chloroperoxybenzoic acid were added. The mixture was then stirred at room temperture for 1 hour and subsequently concentrated, and the resulting N-oxide was purified by column chromatography (silica gel, mobile phase 1:1 methylene chloride/methanol). 2.8 g (80%) of yellow crystals, melting point 105°–108° C. (decomposition), were isolated.

The following substances were obtained similarly to Example 1 and 2 using the appropriate substituted starting compounds:

3. (E),(Z)-1,3-dichloro-10-cyanomethylene-5-(4-methyl-1-piperazinyl)thieno[3,4-b]benzazepine.
4. (E),(Z)-7,8-dichloro-10-cyanomethylene-5-(4-methyl-1-piperazinyl)thieno[3,4-b]benzazepine.
5a. (E),(Z)-7-chloro-10-cyanomethylene-5-(4-methyl-1-piperazinyl)thieno[3,4-b]benzazepine.

Since 5a was prepared similarly to Example 1Aa to 1B starting from m-chlorophthalic anhydride, the 8-chloro derivative was produced in addition to the 7-chloro derivative. Separation by column chromatography (silica gel, mobile phase 85/15 toluene/ethanol) provided the (E) isomer of 5a, melting point 157°–159° C. (ethanol) (nonpolar component) [$^{13}$C NMR, 90 MHz, (DMSO-$d_6$) δ 45.73 (N—CH$_3$); 47.22 and 54.19 (piperazine CH$_2$); 98.06 (=CH—CN); 115.36 (3-C); 116.99 (nitrile); 122.33 (6-C); 129.50 (9-C); 129.85 (1-C); 131.34 (8-C); 134.72 (10a-C); 135.83 (7-C); 136.56 (9a-C); 143.73 (10-C); 154.38 (3a-C); 156.89 (5-c)]; and the Z isomer, melting point 234°–236° C. (ethanol) (polar component) and 5b. (E),(Z)-8-chloro-10-cyanomethylene-5-(4-methyl-1-piperazinyl)thieno[3,4-b]benzazepine.
6. (E),(Z)-1-cyanomethylene-5-(4-ethyl-1-piperazinyl)-thieno[3,4-b]benzazepine.
7. (E),(Z)-10-cyanomethylene-5-(2-ethylamino-1-piperidinylthieno[3,4-b]benzazepine.
5. (E),(Z)-10-cyanomethylene-5-(2-dimethylaminoethylamino)thieno[3,4-b]benzazepine.

EXAMPLE 9

Tablets of the following composition are compressed in a tableting press in a conventional manner.

40 mg of substance of Example 1 (E)
120 mg of corn starch
13.5 mg of gelatin
45 mg of lactose
2.25 mg of Aerosil ® (chemically pure silica in submicroscopically fine distribution)
6.75 mg of potato starch (as 6% paste)

EXAMPLE 10

Sugar-coated tablets of the following composition are prepared in a conventional manner:

20 mg of substance of Example 1 (E)
60 mg of core composition
60 mg of sugar-coating composition The core composition consists of 9 parts of corn starch, 3 parts of lactose and 1 part of Luviskol ® VA 64 (60:40 copolymer of vinylpyrrolidone and vinyl acetate, cf. Pharm. Ind. 1962, 586). The sugar-coating composition consists of 5 parts of sucrose, 2 parts of corn starch, 2 pairs of calcium carbonate and 1 part of talc. The sugar-coated tablets prepared in this way are then provided with an enteric coating.

EXAMPLE 11

10 g of substance of Example 1 (E) in the form of the hydrochloride are dissolved in 5000 ml of water with the addition of NaCl, and the pH is adjusted to 6.0 so that a solution which is isotonic with blood is produced. This solution is dispensed in 5 ml portions in ampules and sterilized.

We claim:

1. A 5-substituted 10-cyanomethylenethieno(3,4-b)-benzazepine of the formula (I):

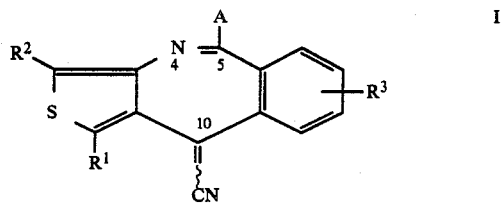

wherein $R^1$ and $R^2$ are each halogen or an alkyl of 1 to 3 carbon atoms; and $R^3$ is hydrogen, halogen or an alkyl group of 1 to 3 carbon atoms; A is —NH$^4$R$^5$, wherein $R^4$ and $R^5$ form, together with the connecting nitrogen atom, a 5- to 7-membered saturated ring, which ring atoms are all carbon or which contain an additional nitrogen or an oxygen atom, wherein said additional nitrogen atom is unsubstituted or is substituted by an alkyl of 1 to 3 carbon atoms, hydroxyalkyl of 2 or 3 carbon atoms, alkoxyalkyl, wherein the alkyl or alkoxy is of 1 to 3 carbon atoms, cycloalkyl or cycloalkylmethyl of 3 to 7 carbon atoms in the cycloalkyl ring, alkynyl of 2 to 5 carbon atoms, and additionally by oxygen in the form of an N-oxide; or A is —NHR$^6$ is aminoalkyl of 2 to 7 carbon atoms, wherein the amine nitrogen atom is unsubstituted or substituted by alkyl of 1 to 5 carbon atoms, or is a constituent of a 5- to 7-membered saturated ring, which ring atoms are all carbon or which contain an additional nitrogen or oxygen atom, wherein said additional nitrogen atom is unsubstituted or substituted by lower alkyl of 1 to 3 carbon atoms or hydroxyalkyl of 2 to 3 carbon atoms; and physiologically-acceptable acid addition salts thereof.

2. The compound as claimed in claim 1, wherein $R^1$ and $R^2$ are each chlorine or fluorine, and $R^3$ is hydrogen, chlorine or fluorine, and A is piperidinyl, piperizinyl or homopiperizinyl which are unsubstituted or substituted on the ring nitrogen by methyl, ethyl, β-hydroxyethyl, cyclopropyl or propynyl, or said ring nitrogen is in the form of an N-oxide.

3. A therapeutic composition for imparting to a patient a sedative, hypnotic, tranquilizer, muscle relaxant, neuroleptic or anti-parkinson effect, which comprises an effective amount of a compound as claimed in claim 1, and a pharmaceutically acceptable excipient.

4. A method of imparting to a patient a sedative, hypnotic, tranquilizer, muscle relaxant, neuroleptic or anti-parkinson effect, which comprises administering to said patient an effective amount of a compound as claimed in claim 1, or the composition as claimed in claim 3.

5. The therapeutic composition as claimed in claim 3, which is in a form suitable for oral or parenteral administration.

6. The method as claimed in claim 4, wherein a daily dose of said compound is from about 1 to 20 mg/kg of body weight for oral administration.

7. The method as claimed in claim 4, wherein a daily dose of said compound is from about 0.1 to 2 mg/kg of body weight for parenteral administration.

* * * * *